(12) United States Patent
Ravnas

(10) Patent No.: US 10,138,409 B2
(45) Date of Patent: Nov. 27, 2018

(54) METHOD FOR MICROBIAL CONTROL OF INJECTION LIQUID FLOW IN A HYDROCARBON RESERVOIR

(71) Applicant: GOE-IP AS, Hafrsfjord (NO)

(72) Inventor: Asle Ravnas, Hafrsfjord (NO)

(73) Assignee: GOE-IP AS (NO)

( * ) Notice: Subject to any disclaimer, the term of this patent is extended or adjusted under 35 U.S.C. 154(b) by 0 days.

(21) Appl. No.: 15/583,261

(22) Filed: May 1, 2017

(65) Prior Publication Data

US 2017/0321106 A1   Nov. 9, 2017

Related U.S. Application Data

(63) Continuation of application No. 14/119,720, filed as application No. PCT/GB2012/051219 on May 31, 2012, now Pat. No. 9,683,162.

(30) Foreign Application Priority Data

May 31, 2011   (NO) .................................. 20110794

(51) Int. Cl.
| | | |
|---|---|---|
| *E21B 43/22* | (2006.01) | |
| *E21B 33/13* | (2006.01) | |
| *C09K 8/50* | (2006.01) | |
| *C09K 8/582* | (2006.01) | |
| *C12N 1/20* | (2006.01) | |
| *E21B 33/138* | (2006.01) | |

(52) U.S. Cl.
CPC ................ *C09K 8/50* (2013.01); *C09K 8/582* (2013.01); *C12N 1/20* (2013.01); *E21B 33/138* (2013.01); *Y02E 50/16* (2013.01)

(58) Field of Classification Search
CPC ........ C12N 1/20; C12N 9/00; C09K 2208/24; C09K 8/582; E21B 33/138
See application file for complete search history.

(56) References Cited

U.S. PATENT DOCUMENTS

| 2,651,500 A | 9/1953 | Teichmann |
|---|---|---|
| 3,332,487 A | 7/1967 | Jones |
| (Continued) | | |

FOREIGN PATENT DOCUMENTS

| CA | 2836390 | 12/2012 |
|---|---|---|
| CN | 103562340 | 2/2014 |
| (Continued) | | |

OTHER PUBLICATIONS

Preliminary Amendment filed on Nov. 22, 2013 with the U.S. Patent and Trademark Office for U.S. Appl. No. 14/119,720, filed Nov. 22, 2013 and granted as now U.S. Pat. No. 9,683,162 dated Jun. 20, 2017 (Inventor- Asle Ravnas; Applicant-Goe IP AS; (7 pages).

(Continued)

*Primary Examiner* — Zakiya W Bates
(74) *Attorney, Agent, or Firm* — Ballard Spahr LLP

(57) ABSTRACT

Disclosed herein are methods of establishing a microbial plug in a hydrocarbon-containing geological formation which has been flooded with water. Also disclosed herein are methods of maintaining such plugs and methods of controlling alteration of the position and/or extent of an established plug. Disclosed herein are plugs such as microbial plugs.

17 Claims, 8 Drawing Sheets

(56) References Cited

U.S. PATENT DOCUMENTS

| | | | |
|---|---|---|---|
| 3,800,872 | A | 4/1974 | Friedman |
| 4,460,043 | A | 7/1984 | Thompson et al. |
| 4,475,590 | A | 10/1984 | Brown |
| 4,485,020 | A | 11/1984 | Shay et al. |
| 4,558,739 | A | 12/1985 | McInerney et al. |
| 4,716,966 | A | 1/1988 | Shu |
| 4,799,545 | A | 1/1989 | Silver et al. |
| 4,800,959 | A | 1/1989 | Costerton et al. |
| 4,905,761 | A | 3/1990 | Bryant |
| 4,947,932 | A | 8/1990 | Silver et al. |
| 5,010,954 | A | 4/1991 | Falk |
| 5,028,344 | A | 7/1991 | Hoskin |
| 5,143,155 | A | 9/1992 | Ferris et al. |
| 5,174,378 | A | 12/1992 | Costerton et al. |
| 5,236,046 | A | 8/1993 | Robison et al. |
| 5,297,625 | A | 3/1994 | Premuzic et al. |
| 9,683,162 | B2 * | 6/2017 | Ravnas ................. C09K 8/50 |
| 2002/0076803 | A1 | 6/2002 | Crews |

FOREIGN PATENT DOCUMENTS

| | | |
|---|---|---|
| EA | 201391785 | 5/2014 |
| GB | 2153834 | 8/1985 |
| GB | 2222420 A | 3/1990 |
| GB | 2246586 | 2/1992 |
| GB | 2368602 | 5/2002 |
| GB | 2383809 | 7/2003 |
| MX | 2013013933 | 7/2014 |
| WO | WO-1992/015771 | 9/1992 |
| WO | WO-2009/129426 | 10/2009 |
| WO | WO-2012/164285 | 12/2012 |

OTHER PUBLICATIONS

Non-Final Office Action dated Feb. 12, 2016 by the U.S. Patent and Trademark Office for U.S. Appl. No. 14/119,720, filed Nov. 22, 2013 and granted as now U.S. Pat. No. 9,683,162 dated Jun. 20, 2017 (Inventor-Asle Ravnas; Applicant-Goe IP AS; (6 pages).

Response to Non-Final Office Action filed on Aug. 8, 2016 with the U.S. Patent and Trademark Office for U.S. Appl. No. 14/119,720, filed Nov. 22, 2013 and granted as now U.S. Pat. No. 9,683,162 dated Jun. 20, 2017 (Inventor-Asle Ravnas; Applicant-Goe IP AS; (11 pages).

Notice of Allowance dated Oct. 21, 2016 by the U.S. Patent and Trademark Office for U.S. Appl. No. 14/119,720, which was filed filed Nov. 22, 2013 and granted as now U.S. Pat. No. 9,683,162 dated Jun. 20, 2017 (Inventor-Asle Ravnas; Applicant-Goe IP AS; (8 pages).

Amendment After Notice of Allowance filed on Nov. 22, 2016 with the U.S. Patent and Trademark Office for U.S. Appl. No. 14/119,720, filed Nov. 22, 2013 and granted as now U.S. Pat. No. 9,683,162 dated Jun. 20, 2017 (Inventor-Asle Ravnas; Applicant-Goe IP AS; (3 pages).

Response to Amendment dated Nov. 25, 2016 by the U.S. Patent and Trademark Office for U.S. Appl. No. 14/119,720, filed Nov. 22, 2013 and granted as now U.S. Pat. No. 9,683,162 dated Jun. 20, 2017 (Inventor-Asle Ravnas; Applicant-Goe IP AS; (2 pages).

Notice of Allowance dated Feb. 14, 2017 by the U.S. Patent and Trademark Office for U.S. Appl. No. 14/119,720, filed Nov. 22, 2013 and granted as now U.S. Pat. No. 9,683,162 dated Jun. 20, 2017 (Inventor-Asle Ravnas; Applicant-Goe IP AS; (5 pages.

Issue Notification dated May 31, 2017 by the U.S. Patent and Trademark Office for U.S. Appl. No. 14/119,720, filed Nov. 22, 2013 and granted as now U.S. Appl. No. 9,683,162 dated Jun. 20, 2017 (Inventor-Asle Ravnas; Applicant-Goe IP AS; (1 page).

Barnard, D. et al. (2010) Extremophiles in biofuel synthesis. Environ Technol. 31: 871-88.

Erbeznik et al. (1997) Clostridium thermocellum JW20 (ATCC 31549) is a coculture with Thermoanaerobacter ethanolicus. Appl Environ Microbiol. 2949-51.

Freier et al. (1988) Characterization of Clostridium thermocellum JW20. Appl Environ Microbiol. 204-11.

Fujiwara, K. et al. (2004) Biotechnological approach for development of microbial enhanced oil recovery technique, Stud Surf Sci Catal. 151:405-45.

Fundamental Techniques of Microbiology (Edition 1), Li Li, Wuhan University of Technology Press, Oct. 31, 2010.

Maity, J. et al. (2011) Effect of cellulolytic gut bacteria as a feed supplement on the growth performance and nutrient digestibility of Asian Seabass. Intl J Aqaut Sci. 2(1):3-15.

Microbial Ecology (Edition 1), Song Fuqiang, Chemical Industry Publishing House, Jun. 30, 2008.

Van Dyk et al. (2009) The cellulolytic and hemi-cellulolytic system of Bacillus licheniformis SVD 1 and the evidence for production of a large multi-enyzme complex. Enzyme Microb Technol. 372-8.

Williams, T.I. et al. (2007) Proteomic profile changes in membranes of ethanol-tolerant Clostridium thermocellum. Appl Microbiol Biotechnol. 74(2): 422-32.

International Search Report and Written Opinion dated Aug. 22, 2012 for International Application No. PCT/GB2012/051219, which was filed on May 31, 2012 and published as WO 2012/164285 on Dec. 6, 2012. Inventor—Ravnas; Applicant—GOE-IP AS) (pp. 1-12).

International Preliminary Report on Patentability dated Dec. 2, 2013 for International Application No. PCT/GB2012/051219, which was filed on May 31, 2012 and published as WO 2012/164285 on Dec. 6, 2012. (Inventor—Ravnas; Applicant—GOE-IP AS) (pp. 1-9).

Preliminary Amendment filed on Nov. 22, 2013 with the U.S. Patent and Trademark Office for U.S. Appl. No. 14/119,720, filed Nov. 22, 2013 and granted as U.S. Pat. No. 9,683,162 on Jun. 20, 2017 (Inventor—Asle Ravnas; Applicant—GOE IP AS; (7 pages).

* cited by examiner

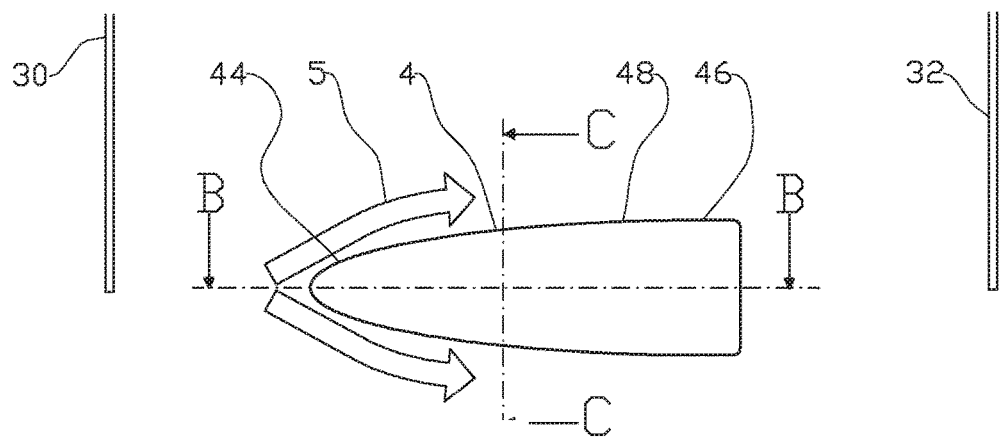
FIG. 6A
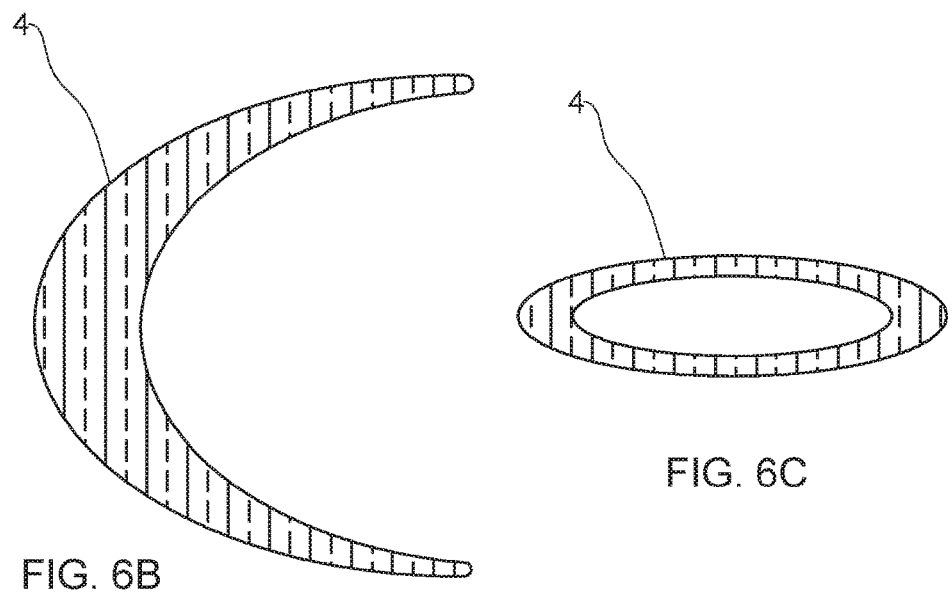
FIG. 6B
FIG. 6C

FIG. 6D
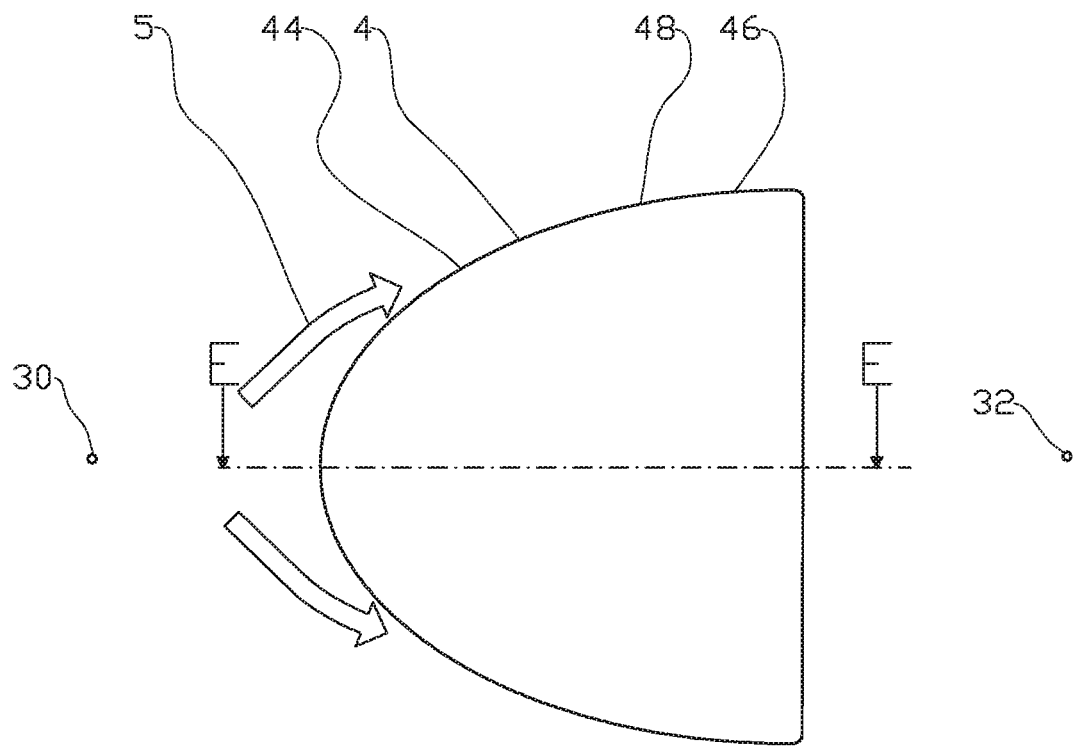
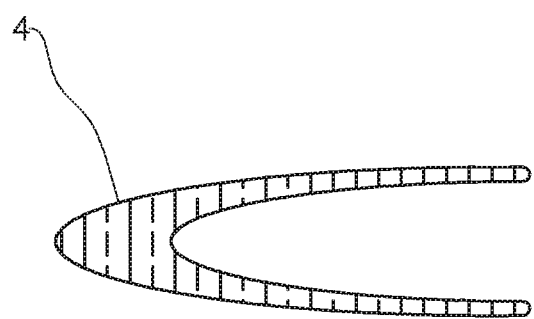
FIG. 6E

METHOD FOR MICROBIAL CONTROL OF INJECTION LIQUID FLOW IN A HYDROCARBON RESERVOIR

CROSS-REFERENCE TO RELATED APPLICATIONS

This application is a continuation of U.S. application Ser. No. 14/119,720 filed Nov. 22, 2013, which is a National Phase application of International Application No. PCT/GB2012/051219 filed May 31, 2012, which claims the benefit of priority to Norwegian Patent Application No. 20110794 filed May 31, 2011. The content of these earlier filed applications is hereby incorporated by reference in their entirety.

The invention relates to a method for forming a plug which reduces or prevents flow of liquid in a hydrocarbon-containing geological formation. More particularly, position and extent of a plug formed by biological activity the invention relates to a method for controlling the in the formation.

It is known in the specialist field in question that liquid can be injected down into a hydrocarbon reservoir in order to increase the degree of recovery, especially of oil, from such a reservoir. Injection liquid is pumped down into the reservoir from one or more injection wells. The injection liquid is intended to flow through the reservoir as far as one or more production wells. The injection liquid is intended to form a hydrophilic front which pushes hydrophobic hydrocarbon, especially oil, before it towards the production well. The injection liquid will also contribute to maintaining the pressure in the formation. The injection liquid will follow a path where the flow resistance is at its least, hereinafter referred to as a flow channel. In the specialist field, this is known as "channelling" or "fingering". It has been found that use of injection liquid increases the degree of recovery, but also that there is still a lot of oil left in the reservoir when the liquid front reaches the production well. The well will then produce with too much water mixed in the oil, making further production unprofitable.

It is possible, to a certain extent, to calculate or model how the injection liquid flows in the reservoir. For example, it is known for low-level radioisotopes with relatively short half-lives to be added as tracers to the injection water. Radiation from the isotopes will be able to be identified in the production well. It is thus possible to estimate the time it takes for the injection liquid to pass through the flow channel from the injection well to the production well. Alternatively, specific chemicals, for example nitrate, can be used as trace substance.

The ability of the injection liquid to force the oil forwards is referred to in the field as the sweep efficiency of the injection liquid. The injection liquid will have this sweep efficiency in the flow channel, but not in areas that surround the flow channel. It is known that the sweep efficiency of the injection liquid can be improved if a plug is formed in the flow channel. The plug can be partially permeable, but the flow resistance increases such that the injection liquid is forced to flow around the plug and thus into those parts of the reservoir that now have the least flow resistance.

The sweep efficiency of the injection liquid is improved in this way. Such plugs can be produced by admixing gel-forming, water-soluble polymers to the injection water. The polymers can be synthetic, for example polyacrylamide, or biological. Xanthan, for example, is used as a biopolymer and is discussed inter alia in patent documents U.S. Pat. No. 4,716,966, U.S. Pat. No. 4,485,020, U.S. Pat. No. 4,947,932, and GB 2,246,586. Patent document U.S. Pat. No. 5,028,344 discusses the use of cellulose and modified cellulose, while patent document U.S. Pat. No. 5,010,954 discusses the use of guar gum and carboxymethylcellulose.

It is also known in the field to add exogenous microorganisms to the reservoir. This is part of what is described as a third-generation technique for enhanced oil recovery, in particular for microbial enhanced oil recovery. This is done by mixing microorganisms, and nutrients for the microorganisms, into the injection liquid. The microorganisms added can form a biofilm in situ. The microorganisms can also form biopolymers in situ, for example xanthan. Individually or in combination, cells, biofilm and polymers can form a plug. Patent document U.S. Pat. No. 4,799,545 teaches the use of a spore-forming, halo-tolerant, thermo-tolerant and facultatively anaerobic bacterium. The bacterium is added to the injection liquid in spore form and is introduced down into the reservoir. Strains of *Bacillus licheniformis* are specifically mentioned as being well-suited for the purpose. Thereafter, sucrose and polyphosphate are added as nutrients to the injection liquid, and it is then conceivable that *B. licheniformis*, on account of cell growth and the exopolymers formed, will produce a plug in the flow channel. Patent document U.S. Pat. No. 5,174,378 discloses isolating bacteria that are naturally present in the reservoir. These are further isolated by their ability to break down selected surfactants. The bacteria can form very small cells when starved, so-called ultramicrobacteria. It is considered that small cells of this kind can more easily penetrate the pore space of the formation. A surfactant-containing foam is injected together with the bacteria. The bacteria return to their active stage, break down the surfactant and produce exopolymers, such that the flow channel is plugged. Patent document U.S. Pat. No. 4,460,043 discloses first adding a suitable bacterium, such as *Leuconostoc* sp., to a reservoir. The bacterium is preferably added while it is in a good state of growth, exponential growth, together with suitable nutrients which maintain the growth but which do not stimulate the bacterium to produce exopolymers. When the bacterium is established at the desired location in the flow channel, sucrose is added to the injection liquid. For certain types of bacteria, sucrose will act as a stimulant that triggers production of exopolymers. It is also proposed to inject the bacteria from the injection well and sucrose solution from the production well. The plug will then be formed where the two streams meet in the reservoir. This will increase the degree of control over how the plug is formed in the flow channel. Patent document U.S. Pat. No. 4,558,739 discloses injecting a nutrient solution that includes molasses, grain wort and malt, for stimulating endogenous bacteria in the flow channel to grow and form, which should in itself increase the flow resistance. In addition, the endogenous bacteria will be able to form exopolymers, which will help in the plug formation. It is proposed to stop the injection for a period of 1 to 10 days in order to increase the effect of the supply of nutrients. The patent document also discloses using strains of *Bacillus* and *Pseudomonas* to plug a flow channel. Patent document U.S. Pat. No. 4,475,590 discloses stimulating endogenous bacteria in an oil-containing reservoir by adding nitrogen and phosphorus to the injection water. The bacteria use the oil as a carbon source, and the bacteria produce fatty acids and fatty alcohols which reduce the surface tension between the injection water and the oil. The bacteria can also produce exopolymers. As examples of suitable types of bacteria, mention is made of bacteria of the genera *Pseudomonas, Achromobacter, Arthrobacter, Flavobacterium, Vibrio, Acinetobacter, Bacillus, Micrococcus* and

*Clostridium*. Patent document U.S. Pat. No. 4,905,761 shows that it is also known that injection of bacteria into a reservoir from an injection well can lead to undesired plugging of the reservoir. The patent document teaches that a microbial formulation comprising types of *Bacillus* and *Clostridium* will produce a mixture of surfactants, such as glycolipids, lipoproteins, polysaccharide-fatty acid complexes, mono- and diglycerides and neutral lipids, and solvents, such as short-chain alcohols, ketones and acids. Such a mixture is advantageous for releasing oil from the reservoir and for transporting oil through the reservoir. The patent document also teaches that types of bacteria of the genera *Acinetobacter, Arthrobacter, Candida, Corynebacterium, Nocardia, Pseudomonas, Rhodococcus* and *Toruloosis* will be able to produce surfactants, while types of bacteria of the genera *Acetobacter, Arthrobacter, Bifidobacterium, Corynebacterium, Gluconobacter, Lactobacillus, Leuconostoc, Pediococcus, Pseudomonas, Ruminobacter, Ruminococcus, Sporolactobacillus, Streptococcus* and *Zymomonas* will be able to produce solvents.

It is therefore known in the field to increase oil recovery from a reservoir by adding nutrients to the injection liquid in order to stimulate endogenous microorganisms to produce biosurfactants and solvents in situ, and to produce biopolymers so as to form a plug. A plug can also be formed when microorganisms in situ increase their cell volume, when supplied with nutrients, and thus block pores in the reservoir. The same effects can also be achieved by adding exogenous microorganisms to the injection liquid, either in the form of spores or as active cells.

Nevertheless, known plugging systems are rather limited and are not widely used in the industry. The present inventor has sought to improve on existing plugging technology. Improvements may include economic benefits, including the cost of raw materials and enhanced oil recovery from a given reservoir which is in the secondary or tertiary oil producing phase. It would be highly desirable if a plug was a dynamic system, able to respond both to control inputs from the surface and to changes in the environment in the reservoir. Changes in the reservoir environment could include changes in the liquid flow around the plug; for example water which had been forced around a plug in a water channel and into adjacent oil containing regions may clear those areas of oil, enabling the plug to expand into those areas and forcing the water to sweep into new oil containing zones further from the original water channel.

After a microbial plug has been established, it may be desirable to change the position of the plug in the reservoir and to change the extent of the plug in a direction between one or more injection wells and one or more production wells. It may also be desirable to change the extent of the plug so as to include more than the original flow channel.

It is also desirable to develop suitable alternatives to molasses and sucrose as nutrients for microorganisms in a reservoir. It is also desirable to develop a viscous nutrient solution that can also increase the sweep efficiency of the injection water.

The object of the invention is to overcome or minimize at least one of the disadvantages of the prior art, or at least to make available a useful alternative to the prior art.

The object is achieved by the features set forth in the description below and in the attached patent claims.

The present inventor has found that by careful selection of the microorganisms for use in the plug, as well as the nutrients supplied to them and methods for their introduction, it is possible to provide an improved, dynamic and self-controlling as well as controllable plug.

The invention exploits the fact that microbial growth can be controlled by increasing or decreasing the availability of nutrients, and that microorganisms can be inactivated or killed with the aid of a suitable biocide. The invention also exploits the fact that the rate of flow of injection liquid with nutrients and without nutrients can be increased, decreased or stopped altogether. The invention further exploits the fact that an established plug will lead the injection liquid into geological formations that surround the flow channel where a plug is established.

The invention also exploits the fact that the injection liquid is colder than the petroleum-containing geological formation. This means that, over time, the injection liquid will cool at least some parts of the geological formation from a temperature that prevents microbial growth to a temperature at which microbial growth is possible. This applies especially if both the quantity of injection liquid and also the flow volume are sufficient. The invention also exploits the fact that a pH regulator can be added to the injection liquid. The regulator can be acidic or basic, and the pH regulator can have buffer capacity. Use is also made of the fact that a pH regulator in the injection liquid can be used up by reacting chemically with components in the reservoir, such that the pH value in the injection liquid will come close to the pH value of the reservoir. Especially if the stream of injection liquid is stopped, the pH regulator will diffuse out of the injection liquid and into the pore water of the reservoir, which has the effect that the pH regulator is diluted and the pH value of the injection liquid, over time, comes close to the pH value of the reservoir. Use is also made of the fact that the injection liquid has, or can have, a lower salt content than the pore water in the reservoir. This means that the salt content in the reservoir, at least in parts of the reservoir, can be reduced from a concentration that prevents microbial growth to a salt content in which microbial growth is possible.

The invention also exploits the fact that micro-organisms can produce metabolites which, in sufficient concentration, have an inhibiting effect on the growth of the organism. Such metabolites can be external and/or secondary metabolites. Ethanol is an example of such a metabolite. Use is also made of the fact that gases, for example $CO_2$, can, at certain concentrations, have a stimulating effect on microbial growth. Use is also made of the fact that many microorganisms cannot grow in the presence of high concentrations of hydrocarbons, especially oil, or on substrates covered by hydrocarbons, but that they can grow there when the concentration of hydrocarbons decreases.

The invention also exploits the fact that the thermophilic bacterium *Clostridium thermocellum* can use cellulose as a carbon source under anaerobic conditions. *C. thermocellum* has cellulosomes and can break down cellulose to cellobiose and cellodextrin, and can break down hemicellulose to xylose, xylobiose and other pentose sugars (Barnard, D. et al., 2010, Extremophiles in biofuel synthesis, Environ. Tech. 31, 871-888 (doi: 10.1080/09593331003710236)). Like other Clostridia, *C. thermocellum* is a spore-forming bacterium.

In the description below, control procedure means any procedure where the purpose of the procedure is to act on the microbial activity in a petroleum-containing geological formation. Without being an exhaustive list and without limiting the invention, a control procedure involves: injecting injection liquid; regulating the quantity and flowrate of the injection liquid; adding salt, nutrients, pH regulator or biocide to the injection liquid to an estimated level; regulating the temperature of the geological formation with the aid of the injection liquid; inducing microbial colonization of surfaces; inducing increased microbial activity or growth; inducing sporulation in spore-forming microorganisms; inducing inactivation or cell death; and inducing production of exogenous metabolites, including biofilm, or exogenous microbial inhibitors of microorganisms.

In the description below, without limiting the invention, microbial activity means at least one of the following activities: aerobic respiration, anaerobic respiration, colonization of surfaces, growth, cell division, sporulation, metabolism, production of endogenous and exogenous primary metabolites, production of endogenous and secondary metabolites, inactivation and cell death. It will be clear from the context which activity is being discussed.

In the description below, microorganisms mean eukaryotic bacteria, archaebacteria and fungi. It will be clear from the context which type of organism is being discussed. Bacteria and Archaea are preferred.

Preferred properties of the microorganisms are defined in the claims. In addition, the microorganisms are preferably facultative anaerobes and are preferably present as a monoculture. The microorganisms ("microbe" is used synonymously with microorganism herein) are typically compatible with reservoir conditions in terms of pH and salinity, although preferably the microorganisms thrive at a pH which is different from normal reservoir conditions but can be readily applied by the injection liquid. Preferably the microorganism produces a secreted product which is inhibitory to growth of the microorganism, e.g. ethanol. While the microorganism cannot use hydrocarbons as a carbon source, they can preferably tolerate oil and more preferably oil is not inhibitory to growth. The microorganisms can preferably grow at a high density and have a cohesion which means the plug can withstand pressure without the need for a strong biofilm. The microorganisms preferably exist in spore form at one or more of, low temperature, starvation and high turbidity, e.g as caused by injection into a reservoir.

The present inventor used a novel set of selection criteria in identifying suitable microorganisms. In particular it was found that suitable candidate microorganisms may be found by selecting for those species which are capable of degrading complex sugars (i.e. using such substrates as a carbon source) and occur naturally in river deltas. As such this group represent a preferred class of microorganisms for use in the methods of the present invention. Either individually or in combination, thermophilicity, oxygen requirements, pH tolerance, ability to degrade hydrocarbons and tolerance towards hydrocarbons, as well as factors affecting dormancy and spore formation may also be taken into consideration in the selection process.

The microorganisms are preferably cellulolytic and/or hemicellulolytic. In reality, most cellulolytic organisms are also hemicellulolytic. Such organisms are able to utilise cellulose or hemicellulose as sole carbon source. In practice they can also use other carbon sources, in particular derivatives and degradation products of these complex polysaccharides, such as the soluble disaccharide cellobiose.

Preferred mircoorganisms according to the invention include *Clostridium thermocellum* and *Acidothermus cellulolyticus*. Different reservoirs are at different temperatures and the microorganisms can be selected accordingly; *A. cellulolyticus* thrives at higher temperatures than *C. thermocellum* and so is more suitable for hotter reservoirs.

In the description below, injection liquid means injected fresh water or injected salt water that is supplied to a geological formation through an injection well. Salt water can include fresh water to which salts are added, a mixture of sea water and fresh water, natural brackish water and undiluted sea water. The injection liquid can be degassed, supplemented with biocides or exposed to radiation in order to reduce the number of microorganisms in the injection liquid. Preferably the injection liquid is less saline than salt water, more preferably the salinity is 3.5-6%.

In the description below, nutrient solution or growth medium means an injection solution that has been supplemented with nutrients for microorganisms. As carbon source or energy source, the nutrients can, for example, contain cellulose, hemicellulose, derivatives of cellulose and hemicellulose, starch, other polysaccharides, oligosaccharides, disaccharides and monosaccharides, a mixture of such saccharides and nutrients containing such saccharides. Preferably the carbon source is soluble. Preferably the growth medium contains a carbon source selected from the group comprising cellulose, hemicellulose, carboxymethyl cellulose, cellobiose, xylose, xylobiose and xylan. Cellobiose is particularly preferred. Sucrose and glucose are generally not suitable.

The nutrient solution can also contain one or more suitable nitrogen sources, phosphorus sources, potassium sources and trace element sources, such as are known in the field. The nutrient solution is a growth-promoting solution for microorganisms. Suitable components of the growth medium, including salts and minerals, are described in the Examples, in particular in Freier medium which represents a suitable growth medium. The growth medium is typically mixed with injection water above ground and the salinity, pH etc. optimised before injection into the reservoir.

In a first aspect, the present invention provides a method of establishing a microbial plug in a hydrocarbon-containing geological formation which has been flooded with water, the method comprising:
  a) introducing into the formation a microbial inoculum, the microorganisms of which are:
    (i) spores or otherwise in a dormant state,
    (ii) capable of sporulation,
    (iii) cellulolytic or hemicellulolytic,
    (iv) thermophiles, extreme thermophiles or hyperthermophiles,
    (v) unable to utilise hydrocarbons as a carbon source, and
    (vi) not indigenous to the hydrocarbon-containing geological formation;
  b) simultaneously or sequentially introducing into the formation a growth medium which provides a carbon source which can be utilised by the microorganisms introduced in step (a) but not by indigenous microorganisms;
  c) exposing the inoculum to conditions which enable the microorganisms to enter an active growth phase within water channels in the geological formation; and
  d) introducing an injection liquid comprising further growth medium as defined in step b) into the formation via an injection well.
  The "water channel" may be a void through solid material, akin to an underground river. Alternatively, a water channel may be a discrete solid layer which acts as a conduit for water flow relative to surrounding solid zones of different composition. Thus, a water channel may be a permeable layer of rock or sandy material.

Preferably the inoculum is in the form of spores. A dormant state may conveniently be caused through starvation of the microorganisms. Without wishing to be bound by theory, it seems that by introducing the inoculum in a sporous or other dormant state, they are more readily disposed into the formation, preferably into water channels within the formation. The inoculum is preferably introduced, together with growth medium, into the formation down an injection well. The flow of liquid into the formation is then reduced or stopped for a period to allow the inoculum to leave the sporous or dormant state and start to grow. Turbid conditions as are caused by normal flow rates of injection fluid inhibit growth. This period of low 'flow' or 'no-flow' may typically be for 12-72 hours, e.g. around 24 hours, sufficient to allow the microorganisms to enter an active growth phase. An active growth phase will be defined, for example, by cell division, increased metabolism and increase in cell size.

Once active cell growth has begun, the microorganisms can tolerate increased liquid flow and, indeed, liquid flow is required for the plug to develop fully as further nutrients are required. Continuous liquid flow from an injection well is then preferred for growth and maintenance of the plug, helping to keep a balance between nutrient input to the plug and removal of any inhibitory products of metabolism such as ethanol. The plug has as its primary purpose a reduction in permeability in the channel where it grows, however, it is preferably still partially permeable, allowing some liquid flow through the plug.

The preferred geological formations are those which contain established water channels before introduction of the inoculum. This can conveniently be determined by a high water content in the output of the production well.

In a further aspect, the present invention provides a method of maintaining a microbial plug in a hydrocarbon-containing geological formation, said plug comprising microorganisms which are:
(i) capable of sporulation,
(ii) cellulolytic or hemicellulolytic,
(iii) thermophilic, extreme thermophilic or hyperthermophilic,
(iv) unable to utilise hydrocarbons as a carbon source, and
(v) not indigenous to the hydrocarbon-containing geological formation;
wherein the formation is flooded with liquid which is injected into the formation through one or more injection wells and flows to one or more production wells, the liquid comprising a growth medium which provides a carbon source which can be utilised by the microorganisms in the plug but not by indigenous microorganisms.

It is described later how the plugging system of the present invention allows for controlled alteration of the plug. More generally, the methods will incorporate phases of maintenance where active steps to alter the position or extent of the plug are not required. However it may still be beneficial to monitor the plug and the impact it is having on the reservoir environment. This is conveniently done by monitoring the output of a production well, for example the oil, water or other chemical content of the output as well as the rate of output and the temperature of the output. As a consequence of the composition or other properties of the output, the concentration of one or more components in the injected liquid or one or more physical properties of the injected liquid may be adjusted. For example, flow rate may be altered, the temperature of the injected liquid may be changed.

Adjustments to the concentration of components include adding a new component or removing a component entirely. Typically changes will be to the amount of the component providing the carbon source to the microorganisms, of other desired nutrients, the salinity of the injected liquid or its pH.

As demonstrated in the Examples, a preferred feature of the plugs of the present invention is that they are removable or substantially removable, for example by cutting off the supply of growth medium. This provides greater flexibility than, for example, a static plug based on introduced polymers or secreted products of microorganisms. The biomass itself is central to the plugging action according to the present technology and this provides a dynamic system which can change in situ in response to reservoir conditions and/or to external control stimuli.

pH is a useful tool in the methods of the present invention. In particular the pH of the injection liquid containing the growth medium is preferably selected such that it is inhibitory for indigenous microorganisms but the introduced microorganisms can grow at that pH.

The source of carbon which is injected into the reservoir provides a similar opportunity for preferential growth of the introduced microorganisms which form the plug. The source of carbon in the growth medium is defined herein and is one which cannot be utilised to any significant extent, i.e. cannot itself support growth, by the indigenous microorganisms who typically use hydrocarbons or glucose or sucrose as a carbon source.

The plug exists, for weeks, months or even longer as a dynamic system in the formation. The plug creates changes in the hydrocarbon zones surrounding the water channel in which the plug is established. The plug receives nutrients in the injected liquid which is preferably provided as a continuous flow, this encourages growth. Growth of the plug is limited by oil in surrounding zones, but as water first drives the oil from those areas due to exertion of pressure caused by the presence of the plug and is then able to flow into those zones changing then from oil-wetted zones to water-wetted zones, so the plug can expand into these areas which are receiving nutrients in the liquid flow.

Temperature is a further self-controlling features to which the dynamic plug responds. Temperatures will increase towards the production wells and, depending on the microorganism, growth in the flow direction will be inhibited above a certain temperature. The microorganisms are also inhibited by too high a flow rate and this provides a mechanism of self-adjustment and top-down control. In general, a parabolic shape to the plug with tails (alternatively considered as a curved funnel which is partly hollow inside) as shown in the figures, is thought to be highly beneficial and to provide or enhance the functionality of the plugs of the invention; the plugs preferably have such a shape. The shape may be a function of the availability of nutrients within the plug due to the semi-permeability thereof and to the production of inhibitory molecules by the microorganisms.

Preferred microorganisms possess a cellulosome which may contribute to the permeability and cohesiveness of the plug, as well as to the digestion of the carbon source.

In a further aspect, the invention relates to a method for controlled alteration of the position and/or extent of an established microbial plug in a hydrocarbon-containing geological formation through which an injection liquid can flow from one or more injection wells to one or more production wells, which method comprises selecting a microbial inoculum, an injection liquid and a growth-promoting liquid for formation of a microbial plug, and which method further comprises using at least one control procedure selected from a group comprising pH regulation, temperature regulation, liquid quantity regulation, gas quantity regulation, inhibitor regulation, nutrient quantity regulation, salinity regulation, viscosity regulation, pressure regulation, flowrate regulation, and addition of further microorganisms to the injection liquid.

The abovementioned method can be used for controlled movement of the established plug in a direction towards at least one production well, in which the plug can be formed by at least one type of spore-forming microorganism, and which method can comprise:
- using a control procedure to stimulate the microorganism to form spores;
- using a control procedure to move the microbial spores in the geological formation; and
- using a control procedure to activate the microorganism to break out of the spores and become active. The control procedure for stimulating the microorganism to form spores can comprise reducing the nutrient supply. In an alternative embodiment, the control procedure for stimulating the microorganism to form spores can comprise pH regulation of the injection liquid.

The abovementioned method can be used for controlled lengthening of the established plug in a direction towards at least one injection well, where the method can comprise:
- the control procedure of supplying fresh nutrients to a plug front; and
- the control procedure of reducing the flowrate of the injection liquid or stopping it completely, such that the microorganism can grow into a zone containing nutrients between the plug front and the injection well.

The method can further comprise the control procedure of supplying a gas to the injection liquid in order to stimulate the microbial activity in the plug front. The gas can be $CO_2$.

The abovementioned method can be used for controlled expansion of the spread of the established plug at the flanks of the plug, where the method can comprise:
- the control procedure of supplying fresh nutrients to the injection water flowing along the flanks of the established plug; and
- the control procedure of reducing the flowrate of the injection liquid or stopping it completely such that the microorganism can grow into a zone containing nutrients at the flanks of the plug.

The abovementioned method can be used for controlled movement of the established plug front in a direction towards at least one of the production wells, where the method can comprise:
- using a control procedure to supply biocides to the injection water to a growth-inhibiting or lethal level.

In an alternative embodiment, the method for controlled movement of the established plug front in a direction towards at least one of the production wells can comprise:
- using a control procedure to regulate the pH of the injection water to a growth-inhibiting or lethal pH level such that microbial activity ceases in the plug front facing towards the injection well.

The abovementioned methods in the various embodiments in accordance with any of the preceding claims, where the methods can further comprise
- locating an isolated hydrocarbon-containing section in the geological formation where the permeability is less than the permeability of the plug and greater than the permeability in an established flow channel; and
- positioning the plug to surround the isolated hydrocarbon-containing section such that the injection liquid flows through the isolated hydrocarbon-containing section.

In a further embodiment, the method can comprise adding to the injection liquid, at the desired concentration, biopolymers selected from a group comprising cellulose, hemicellulose, derivatives of cellulose, and derivatives of hemicellulose.

The abovementioned regulation of the viscosity can comprise adding to the injection liquid, at the desired concentration, biopolymers selected from a group comprising cellulose, hemicellulose, derivatives of cellulose, and derivatives of hemicellulose.

The method described above can further comprise the control procedure of adding a culture of a strain of *Clostridium thermocellum* to the fresh nutrient liquid.

The method described above can further comprise pretreating the section at the plug front or at the flank of the plug by at least one of the following control procedures:
- flooding the plug front or the flank of the plug with injection liquid containing biocide, in order to reduce the quantity of active endogenous microorganisms;
- flooding the plug front or the flank of the plug with injection liquid containing a pH regulator, in order to improve the growth conditions for desired microorganisms;
- flooding the plug front or the flank of the plug with injection liquid of low salt content, in order to reduce the salinity in the pore water in the geological formations that surround the plug front and the flank of the plug, so as to improve the growth conditions for desired microorganisms; and
- flooding the plug front or the flank of the plug with injection liquid in order to cool the geological formations that surround the plug front and the flank of the plug, so as to improve the growth conditions for desired microorganisms.

The method described above can further comprise maintaining the shape of the plug front, the shape of the flank and the shape of a plug tail by flooding the plug with a nutrient solution, and such that microorganisms in the plug form a microbial inhibitor. The microbial inhibitor can comprise ethanol.

In a further aspect, the invention relates to a microbial plug formed in a petroleum-containing geological formation, where the plug comprises microorganisms of the type defined above, preferably *Clostridium thermocellum*. Preferably the formation is water flooded.

In a further aspect, the invention relates to an injection liquid for flooding a petroleum-containing geological formation, where the injection liquid contains a polymer selected from a group comprising cellulose, hemicellulose, derivatives of cellulose, and derivatives of hemicellulose.

In a further aspect, the invention relates to use of microorganisms of the type defined herein, preferably *Clostridium thermocellum*, for formation of a microbial plug in a petroleum-containing geological formation. Preferably the formation is water flooded.

Preferred embodiments are described below by way of example and are depicted in the attached drawings, in which.

Figure 2:
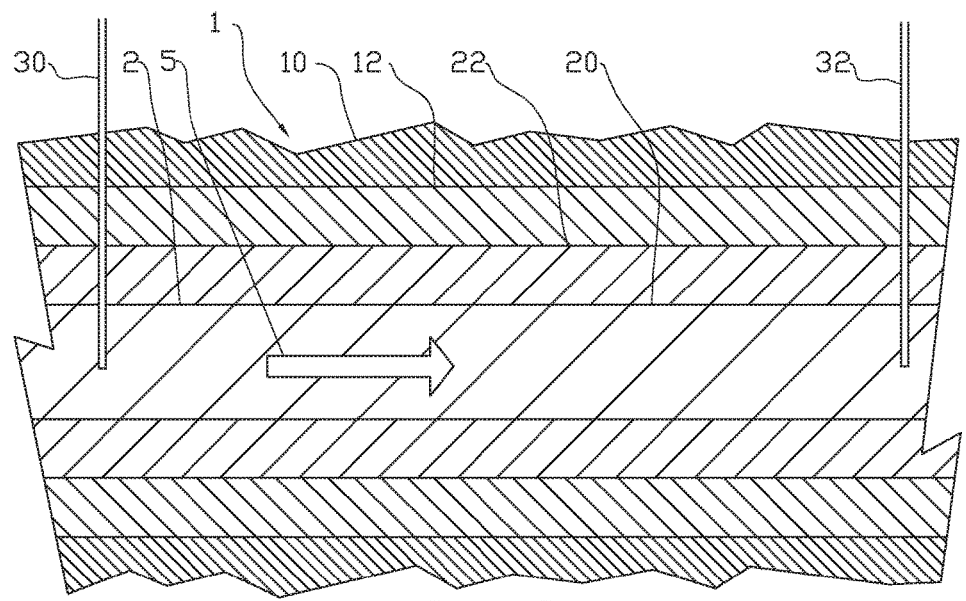
FIG. 2 shows schematically, and seen from the side, a hydrocarbon-containing geological formation where a flow channel is formed between an injection well and a production well, as is known in the field.
Figure 4:
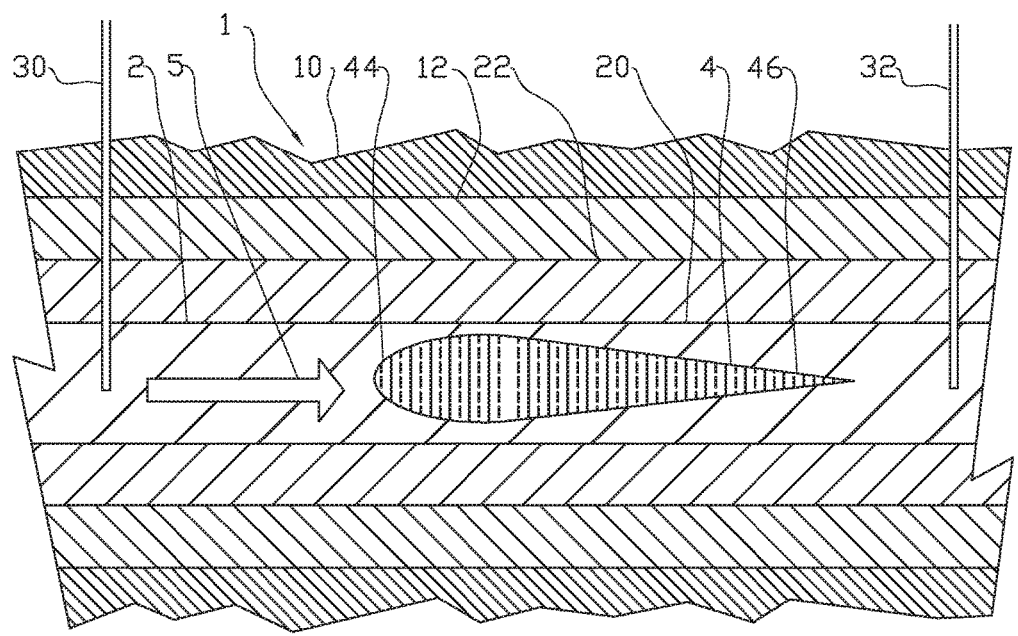
Figure 5:
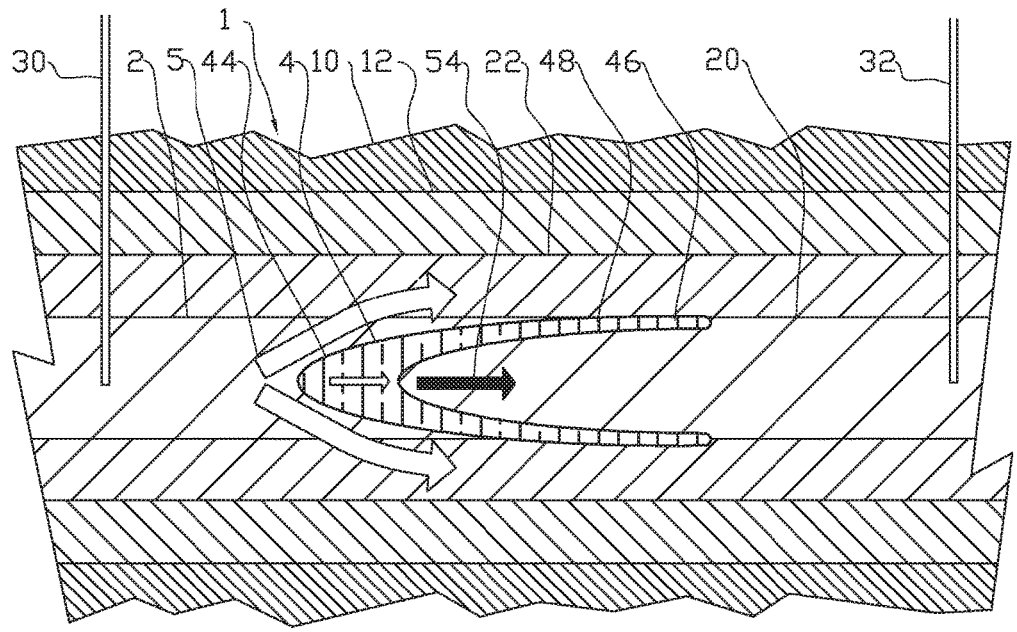
Figure 7:
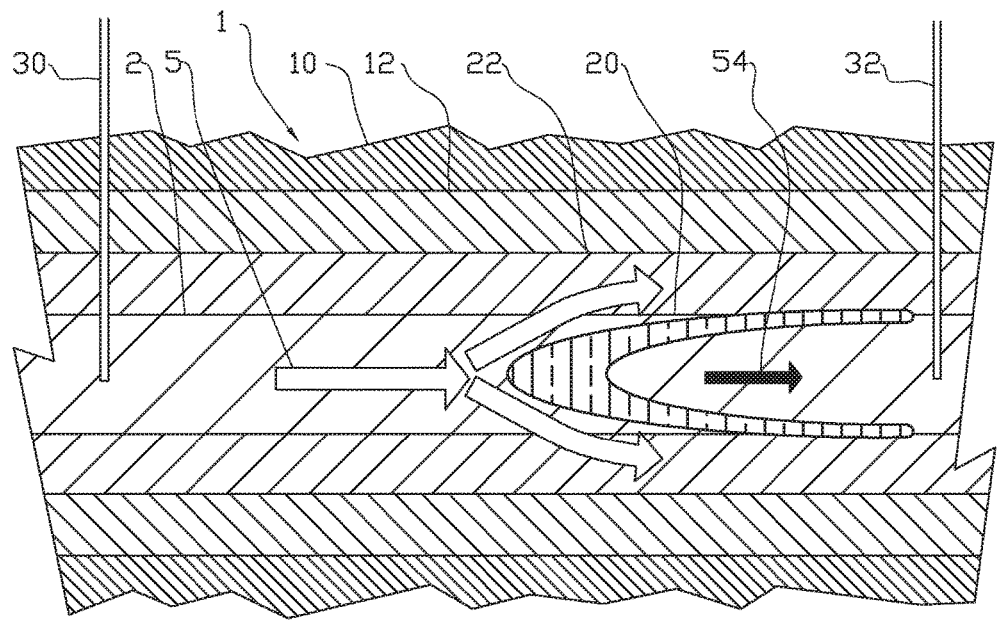
Figure 8:
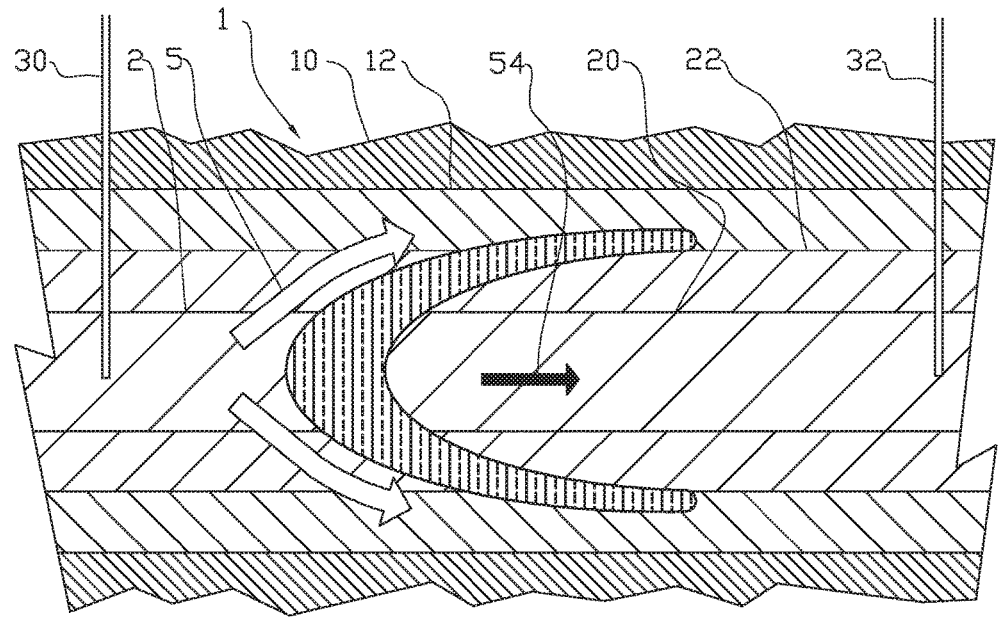

FIGS. 3A-D show schematically and on a microscopic scale: A) how hydrocarbons fill the pore space in a geological formation; B) colonization of the pore space with microorganisms; C) plugging of the formation with microorganisms; and D) shrinkage of the microbial biomass as a result of lack of nutrients, and opening of the pore volume for through-flow, as is known in the field;

FIG. 4 shows, at the same scale as FIG. 2, how a microbial plug is formed in the flow channel, as is known in the field;

FIG. 5 shows, at the same scale as FIG. 2, how a type of microbial plug different from that shown in FIG. 4 is formed in the flow channel;

FIGS. 6A-6E show a schematic side view and cross sections of a plug, where the plug's production of inhibiting metabolites leads to a reduced activity or biomass in the section of the plug towards a production well; A) is a schematic representation of the external shape of such a plug 4 seen from the side; B), C) and E) cross sections that schematically depict the effect of the inhibitor liquid stream 54 on the internal shape of the plug 4; and D) plug from above;

FIG. 7 shows the extent of a microbial plug towards a production well after movement of the plug;

FIG. 8 shows a microbial plug with a greater extent towards the flank of the plug;

FIGS. 9A-9D show a highly schematic representation of the phases in the movement of a plug with a direction of flow of injection liquid towards a production well; A) the established plug 4, and the injection liquid stream 5 that sweeps along the flanks 48 of the plug 4; B) a schematic showing that spore-forming microorganisms 8, which form the plug 4, sporulate for lack of nutrients; C) how the injection liquid stream 5 will move the sporulated microorganisms 8 towards the production well 32; and D) how plug 4 is formed; and in FIGS. 10A-D, A-B are schematic representations of the phases in the elongation of a plug towards an injection well counter to the direction of flow of injection liquid, and Figures C-D show a shortening of the plug's tail.

Figure 1:
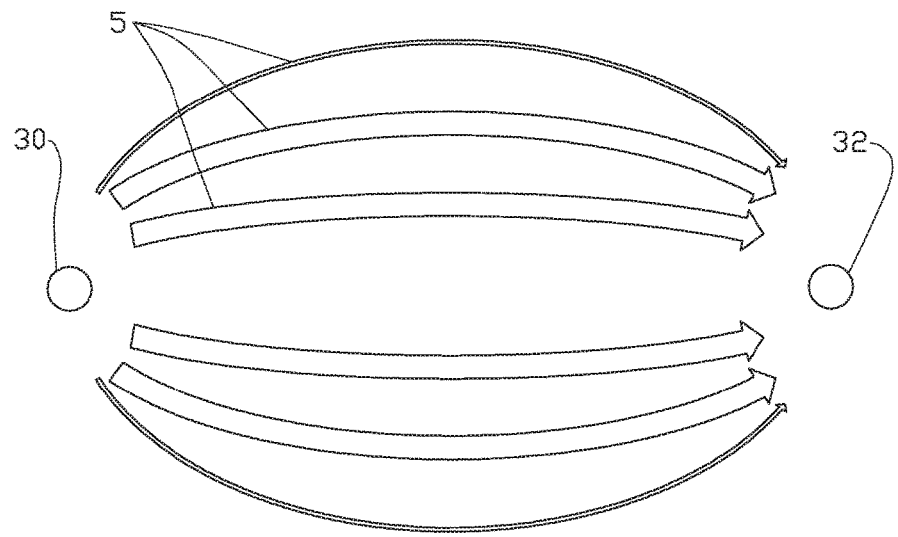
FIG. 1 shows schematically, and seen from above, how an injection liquid flows between an injection well and a production well in a geological formation, as is known in the field.

In the figures, reference number 1 designates a geological formation that surrounds a hydrocarbon-containing reservoir. The reservoir 1 is divided schematically into zones: a zone with low permeability 10, a zone with greater permeability 12, and a flow channel 2. The flow channel 2 is formed in a zone where the reservoir 1 has high permeability and an injection liquid has flowed through the flow channel 2. The flow channel 2 is divided into a central zone 20 and a peripheral zone 22. Injection liquid is introduced into the reservoir 1 in a manner known per se through an injection well 30. Hydrocarbons and possibly other liquid is recovered from the reservoir 1 from a production well 32. The figures indicate one injection well 30 and one production well 32. This is schematic and is to be understood as meaning that there can be one or more injection wells 30 and one or more production wells 32. An injection liquid stream 5 flows through the flow channel 2. As is shown in FIG. 1, the injection liquid can follow several channels and the quantity of injection liquid flowing through the flow channel is dependent among other things on the flow resistance. This is shown in FIG. 1 by different widths of the arrows that indicate the injection liquid stream 5. FIG. 4 shows a microbial plug 4 in the reservoir 1, which plug 4 is formed in a manner known per se.

FIG. 3 shows schematic representations of an assumed mechanism or explanatory model for drainage of hydrocarbons 7 that are located in a pore volume between solid minerals 6, without limiting the invention to this model. FIG. 3A shows that hydrocarbon 7 fills the pore volume between the minerals 6. Many types of microorganisms 8 cannot grow or live in such hydrocarbon-filled pore spaces. FIG. 3B shows that remains of the hydrocarbon 7 are still present between the minerals 6 after the reservoir 1 has produced hydrocarbon 7, possibly after injection liquid has flowed through the reservoir 1 in a known manner. FIG. 3B also shows that microorganisms 8 are added between the minerals 6. The microorganisms 8 can form colonies 82 when they are supplied with nutrient in a nutrient liquid stream 52. The microorganisms 8 will grow, and the colonies 82 will plug the pore volume between the minerals 6, as is shown in FIG. 3C. This will force the injection liquid stream 5 to move around the plug flanks 48, as is shown in FIGS. 5-9. The reduced flow through the plugged part of the reservoir 1 decreases the nutrient availability to the microorganisms 8. After the active growth phase, the microorganisms 8 will enter the terminal phase and die or sporulate if the microorganism 8 is a sporulating microorganism 8. The volume of the biological material decreases, and this part of the reservoir 1 becomes more permeable, as is shown in FIG. 3D and indicated, for example, in FIG. 5. Residues of hydrocarbon 7 can be released from the minerals 6 with the aid of solvents, surfactants and mixtures thereof, and they are conveyed with the injection liquid to the production well 32. This increases the degree of recovery of hydrocarbon 7 from the reservoir 1. Solvents and/or surfactants can be added to the injection liquid. Solvents and/or surfactants can be produced in situ by microorganisms 8 in the reservoir 1.

FIG. 4 is a schematic representation of a plug 4 in the flow channel 2. The plug 4 is formed by microbial activity and consists of microorganisms 8 and biopolymers. The plug 4 can be formed by nutrients in the injection liquid being supplied to the flow channel 2. There will then be nutrients present along a part of the flow channel 2. Thereafter, exogenous microorganisms 8 in the injection liquid are supplied to the flow channel 2. Supply of injection liquid is stopped after a time, and the microorganisms 8 colonize surfaces in the pores and hollow spaces of the reservoir 1. Since the pores of the reservoir 1 will have a certain filter effect, there will be a greater inoculum of cells at the front 44 of the plug nearer to the injection well 30 in relation to the production well 32, as is indicated in FIG. 4. Over time, the microorganisms will spread towards the production well 32 since there are nutrients in this area. Production from the production well 32 will also contribute to flows in the reservoir 1 towards the production well 32. This is indicated in FIG. 4 as a tail 46 in the direction of the production well 32. The density of microorganisms 8 will be greater at the centre 20 of the flow channel 2 than at the periphery 22. The plug 4 can also be established by injecting microorganisms 8 and nutrients at the same time. The plug 4 can also be established by first injecting microorganisms 8 and then nutrients. In this case, the microorganisms 8 nearest the injection well 30 will consume nutrients, such that there are fewer nutrients available in the flow channel 2 towards the production well 32. The plug 4 is partially permeable, but some of the injection liquid will flow towards the production well 32 in the geological formation 1 along flanks 48 of the plug 4. The injection liquid stream 5 will thus carry hydrocarbons with it along the flanks 48 of the plug 4 into peripheral areas 22 of the flow channel 2 and into the geological formation 12 of lower permeability.

FIG. 5 shows a microbially formed plug 4 according to the invention, where the plug 4 produces an extracellular inhibitor, which forms an inhibitor liquid stream 54 in the direction towards the production well 33. FIG. 6A is a schematic representation of the external shape of such a plug 4 seen from the side, FIG. 6D shows such a plug seen from above, while FIGS. 6B, 6C and 6E are cross sections that schematically depict the effect of the inhibitor liquid stream 54 on the internal shape of the plug 4. Microorganisms 8 at the flank 48 and tail 46 of the plug 4 obtain nutrients, for maintaining their activity, from the nutrient liquid stream 52 that flows along the flank 48 and the tail 46.

Figure 9A:
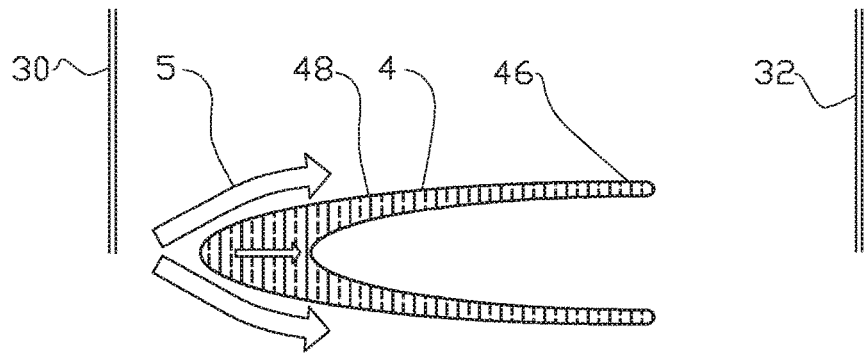
Figure 9B:
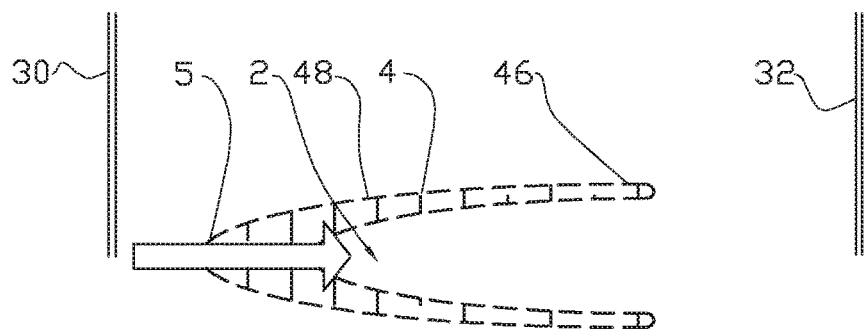
Figure 9C:
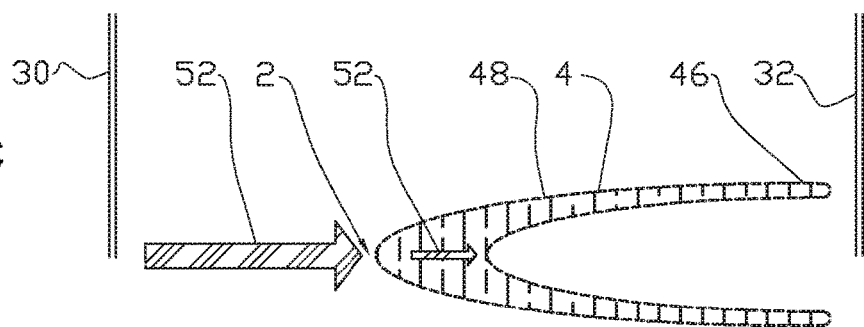
Figure 9D:
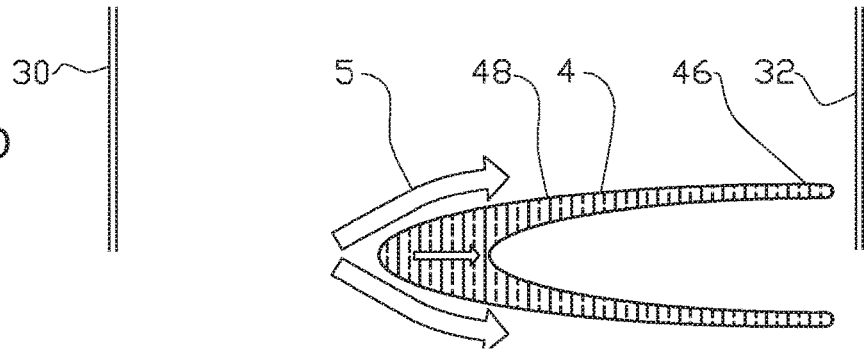

FIGS. 9A-D show schematically, in a more simplified form and in more detail, how the microbially formed plug 4 can be moved towards the production well 32, as indicated in FIG. 7. FIG. 9A shows the established plug 4, and the injection liquid stream 5 that sweeps along the flanks 48 of the plug 4. FIG. 9B shows schematically that spore-forming microorganisms 8, which form the plug 4, sporulate for lack of nutrients. This is shown as a stippled outline. The permeability in the plug 4 increases, and the injection liquid stream 5 flows in the original flow channel 2. The injection liquid stream 5 will move the sporulated microorganisms 8 towards the production well 32, as shown in FIG. 9C. Nutrients are supplied to the injection liquid, and a nutrient liquid stream 52 flows through the flow channel 2 and stimulates the microorganisms to break out of the spore stage and become active, such that a plug 4 is formed as shown in FIG. 9D.

Figure 10A:
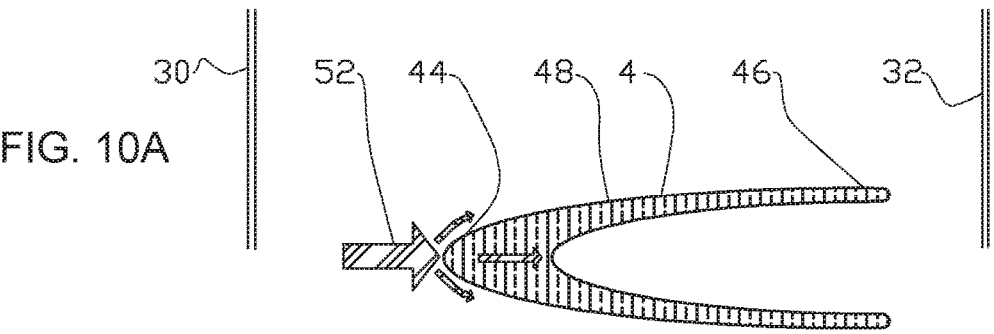
Figure 10B:
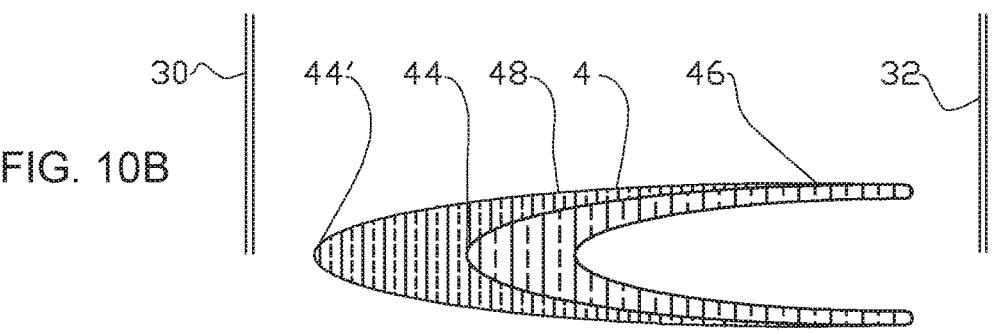
Figure 10C:
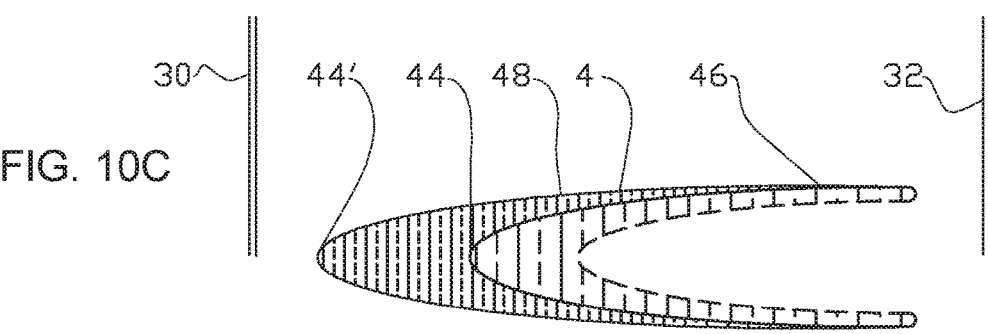
Figure 10D:
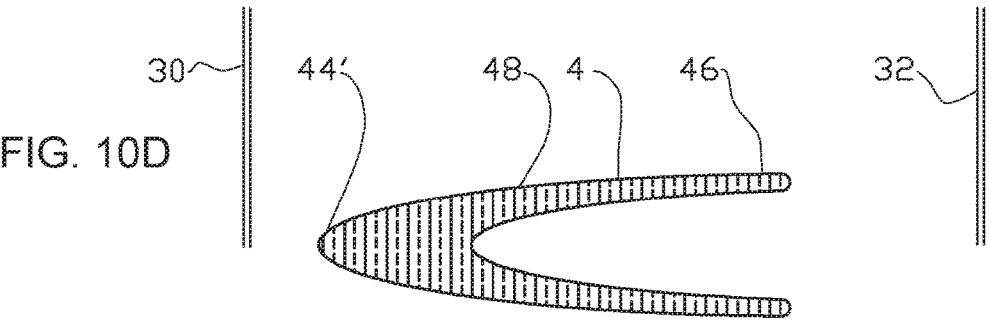

FIG. 8 shows that the flank 48 of the microbially formed plug 4 has expanded towards the more hydrocarbon-rich zones 10, 12 in accordance with the method of the invention. FIG. 10 shows schematic representations of how the front 44 of the microbially formed plug 4 can be moved towards the injection well 30 in accordance with the method of the invention. As is shown in FIG. 10A, a nutrient stream 52 will flow from the injection well 30 towards an established plug 4 in accordance with the invention. Some of the nutrient liquid solution 52 will flow along the front 44 of the plug 4, while some of the nutrient stream 52 will flow through the partially permeable plug 4. The supply of nutrients maintains the microbial activity of the plug 4. The nutrient liquid solution 52 is stopped, such that there are nutrients in contact with the front 44 of the plug, and nutrients extend from the front 44 of the plug 4 and in the direction towards the injection well 30. The plug 4 will form a front 44', which spreads towards the injection well 30, as is shown in FIG. 10B. FIG. 10C shows that microorganisms 8 in the part of the plug 4 facing towards the production well 32 will decrease in activity, sporulate or die over time, because of lack of nutrients. FIG. 10D shows the shape and position of the active part of the plug 4 after a period of time. The plug 4 has thus moved to a position closer to the injection well 4.

EXAMPLE 1

A microbial plug 4 in a permeable geological formation 1 with a flow channel 2 is formed in a manner known per se, by injecting a nutrient solution and a bacterial culture into the formation 1 from an injection well 30. The nutrient solution and the bacterial culture can be injected as one mixture in one pulse, and the pulse is followed by injection liquid without nutrients and bacterial culture. The bacterial culture consists of one or more strains of a spore-forming type of bacteria or several types of spore-forming bacteria. The bacterial culture can consist of a strain of *Clostridium thermocellum*.

Based on the known porosity of the geological formation 1 and the flow characteristics in the flow channel 2, it is possible to calculate when the mixture of nutrient solution and bacteria 8 will reach the part of the flow channel 2 where it is desirable to establish a plug 4. The injecting of injection liquid is halted such that the bacteria 8 are able to establish themselves. The bacteria 8 will use the nutrients for cell division and for general metabolism, which also includes formation of exogenous products, for example a biofilm, and for formation of secondary metabolites, which can include alcohols, aldehydes, ketones and gases. The bacteria 8 will grow in that part of the flow channel 2 where nutrients are available. Facultatively anaerobic bacteria 8 will form an anaerobic environment and are not dependent on the presence of oxygen.

The increased number of bacteria 8, possibly together with biofilm production, will reduce the permeability of the flow channel 2, as is known in the field and is shown in FIG. 3. When the plug 4 is considered to be established, the injecting of injection liquid is recommenced. At the front 44 of the plug 4, that is to say the part of the plug 4 facing towards the injection well 30, the injection liquid will flow mainly around the front 44 of the plug 4 and along the flanks 48 of the plug 4 where the permeability is greater than inside the plug 4. This has the effect that the injection liquid entrains hydrocarbons 7 into parts of the formation 1 that lie outside the original flow channel 2, as is shown in FIGS. 5-9.

Figure 3A:
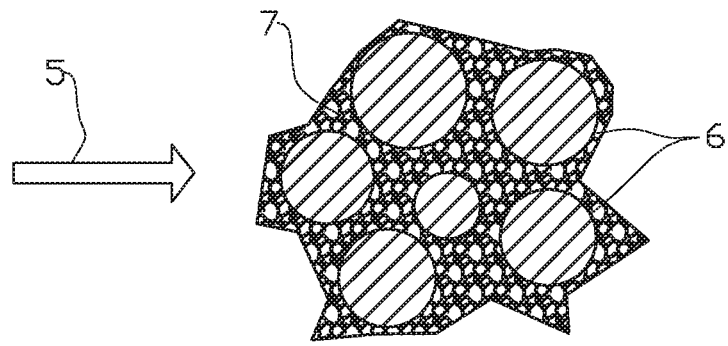
Figure 3B:
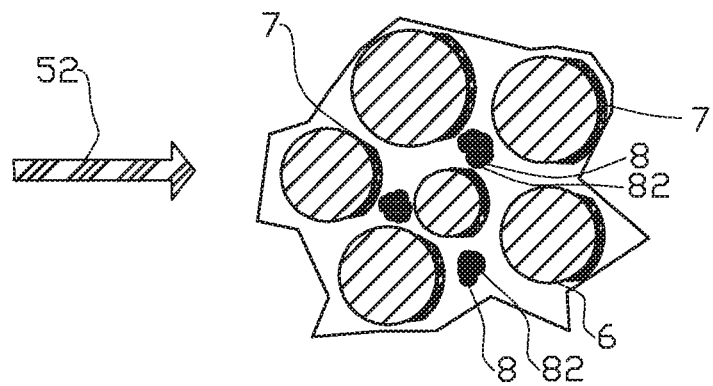
Figure 3C:
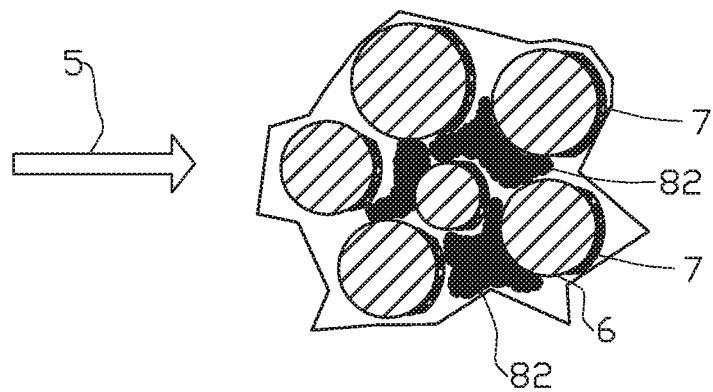
Figure 3D:
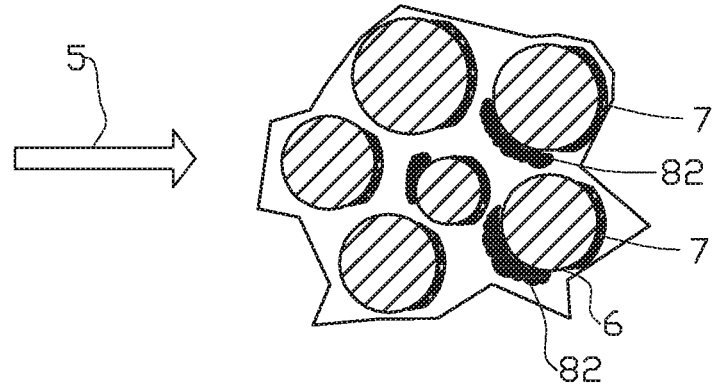

Without supply of fresh nutrients, the bacteria 8 will stop growing and will gradually sporulate as shown in FIGS. 3D, 9B and 10C. The spores are much smaller than the active cells and do not plug the pores in the geological formation 1 in the same way. The pressure applied by the injection liquid against the front 44 of the plug 4 will press or wash the spores along the flow channel 2 such that they penetrate inside the formation 1, which leads to the front 44 of the plug 4 being moved towards the production well 32, as shown in FIG. 9C. A plug 4 that has been established by injection of a mixture of nutrients and microorganisms will have approximately the same nutrient status over the whole extent of the plug 4. When the supply of nutrients is stopped, sporulation will take place more or less simultaneously over the whole plug 4. The front 44 and tail 46 of the plug 4 are in fluid communication, such that the spores in the tail 46 of the plug 4 will also penetrate inside the formation 1 when the spores at the front 44 of the plug 4 begin to penetrate inside. Nutrients are added to the injection liquid, which now once again flows mainly through the flow channel 2, and the nutrients will cause the microorganisms 8 to break out of the spores and form active cells. This has the effect that the whole plug 4 is moved towards the production well 32.

In another embodiment, as an alternative or addition to inducing sporulation by starving, the injection liquid can be provided with acids or bases, which respectively acidify and raise the pH of the injection liquid to a level that induces sporulation. Sporulation will then start at the front 44 of the plug 4 and, as the sporulation begins, the injection liquid will pass further into the original plug 4 and lead to further sporulation. At the same time, the part of the plug 4 containing active microorganisms 8 will counter the flow of the injection liquid in the flow channel 2. The injection liquid is thus forced out along the flanks 48 to the remaining part of the plug 4 and also carries with it, to the flanks 48, spores from the front 44 of the plug. The concentration of the pH regulator of the injection liquid will decrease, because of dilution and chemical reactions, to a level that does not alter the activity of the cells. Thus, the cells in the tail 46 of the plug 4 will not sporulate. By adding nutrients to the injection liquid, the spores in the front 44 and flank 48 of the plug 4 will break out of the spores and form active cells. This has the effect that the front 44 of the plug 4, but not the tail 46, is moved closer to the production well 32, and that the front 44 of the plug 4 is expanded in the peripheral direction.

In an alternative method for moving a plug 4 in the direction from the injection well and towards the production well 32, the nutrient solution is injected first, and the microorganisms 8 are injected immediately thereafter, such that there is contact between the injection liquid with nutrients and the injection liquid with microorganisms. When the injection is stopped, the microorganisms will spread inside the flow channel 2 where there are nutrients. The microorganisms 8 will starve and will sporulate in those parts of the injection channel 2 where the nutrients have been used up. This has the effect that the whole plug 4 moves towards the production well 32 over time.

In another alternative method, a suitable biocide, for example ammonia, is added in a suitable quantity to the injection liquid. This will first inactivate or kill the microorganisms 8 in the front 44 of the plug 4. The effect of the ammonia will abate over time as it reacts with the minerals 6 in the reservoir 1 and is diluted. The result is that the front 44 is moved in the direction towards the production well 32. The microorganisms 8 in the tail 46 of the plug will continue growing and will spread along the flow channel 2 towards the production well 32.

EXAMPLE 2

A microbial plug 4 is established in the manner described in Example 1. After the plug 4 is established, a fresh solution of nutrients is injected as far as the plug front 44. The pumping-in of the injection liquid is stopped when the nutrient solution is in contact with the plug front 44. The bacteria 8 in the plug 4 will grow into the zone with fresh nutrient solution and move the plug front 44 towards the injection well 32, as is shown in FIG. 10B, such that a new plug front 44' is formed. The original plug 4 is partially permeable, such that a proportion of the fresh nutrient liquid stream 52 will penetrate into the original plug front 44 and onwards to the tail 46 of the plug. However, the nutrients will be consumed in the plug 4, such that the original front 44 of the plug 4 is maintained, while little or no fresh nutrients will reach the tail 46 of the plug, and microorganisms 8 in the tail 46 will become inactive, sporulate or die, as shown in FIGS. 10C and 10D. Alternatively, a mixture of microorganisms 8 and fresh nutrients can be injected until it is in contact with the plug front 44. A new plug front 44' will then be established close to the injection well 30. When the new plug front 44' is established, injection liquid is injected and will entrain hydrocarbons 7 around the plug 4. As the nutrients are used up, microorganisms 8 in the tail 46 of the plug 4 facing towards the production well 32 will become inactive, sporulate or die and will reduce the extent of the plug 4 in this direction. This has the effect that the plug 4 is moved towards the injection well 30 over time.

In an alternative embodiment, $CO_2$ can be added to the injection liquid, which is pulsed forwards to the plug 4. $CO_2$ will stimulate growth of certain types of bacteria, for example *C. thermocellum*.

In an alternative embodiment, the direction of flow of the injection liquid is reversed by means of injection liquid being injected from the production well 32 towards the injection well 30. The method is then the same as described in Example 1.

EXAMPLE 3

A microbial plug 4 is established in the manner described in Example 1. The injection liquid will carry hydrocarbons 7 from the geological formations 1 along flanks 48 of the plug 4. When these formations 1, which surround flanks 48 of the plug 4, are drained of hydrocarbons 7 and become more permeable and are more easily colonized by microorganisms 8, nutrients are added to the injection liquid. When the injection liquid with nutrients surrounds at least parts of the flanks 48 of the plug 4 (see FIG. 10A for example), the injection is stopped. Microorganisms 8 from the plug 4 will grow into the zones with fresh nutrient solution and extend the range of the plug 4 along flanks 48 of the plug 4. The injection is then started up again, and the injection liquid will be forced into zones surrounding the extended plug and containing hydrocarbons, such that these are swept out as shown in FIG. 8.

In an alternative embodiment, microorganisms 8 and nutrients are added to the injection liquid flowing past the flanks 48 of the plug 4. When the injection liquid with nutrients surrounds at least parts of the flanks 48 of the plug 4, the injection is stopped. This has the advantage that the expansion of the flanks 48 of the plug 4 takes place more rapidly.

The fresh nutrients in the injection liquid surrounding the plug 4 along the flank 48 and the tail 46 will partially diffuse into the established plug 4 and will contribute to the latter being maintained in these parts.

When the plug 4 is well established, the injection liquid stream 5 will flow past the plug 4 along the plug flank 48 and will sweep hydrocarbons 7 towards the production well 32, as is shown in FIG. 8. This means that the flow channel 2 is expanded. By adding nutrients to the injection liquid and, after a suitable period of time, stopping the supply of injection liquid, microorganisms 8 in the plug 4 will grow into the zones 10, 12 flanking the original flow channel 2.

EXAMPLE 4

A microbial plug 4 is established in the manner described in Example 1. Injection liquid flows along the plug flank 48 and the tail 46 and, over time, will sweep out hydrocarbons 7 in the geological formations that surround the plug 4. The injection liquid will also cool these surrounding geological formations in the reservoir 1. Draining the pores of hydrocarbon 7, in combination with cooling, makes it possible for the microorganisms 8 to colonize areas around the tail 46 and lengthen the tail 46 towards the production well 32 when nutrients are supplied to the injection liquid and these nutrients flow past the tail 46 towards the production well 32. The plug 4 is maintained by means of the microorganisms 8 undergoing alternating phases of growth and shrinkage, as has been described above in connection with FIG. 3. In the shrinkage phase (see FIG. 3D), nutrients can be supplied to the plug 4, and the microorganisms 8 are stimulated to new growth, as shown in FIG. 3C. This has the effect that the plug front 44 is kept stationary, while the extent of the plug 4 towards the production well 32 is lengthened.

EXAMPLE 5

A microbial plug is established in the manner described in Example 1, and the front of the plug is moved towards the injection well, as described in Example 3. In addition, the extent of the plug towards the production well is maintained by pulsing nutrients into the plug 4, as described above, in order to maintain the microbial activity in the part of the plug 4 facing towards the production well 32. The shape of the plug 4 is thus maintained as shown schematically in FIG. 10B.

In FIGS. 5-10, the plug 4 is shown schematically with a hollow portion brought about by in situ production of inhibitors. *C. thermocellum* is an example of a microorganism 8 that produces ethanol. The ethanol concentration will increase through the plug and will, above a given level, have an inhibiting effect for microorganisms 8 downstream. These will be inactivated, sporulate or die. This has the advantage that the outside of the plug 4 (front 44, flank 48 and tail 46) will keep its position at the same time as the active volume of the plug 4 is reduced in proportion to a "compact" plug 4. The requirement of the plug 4 for nutrients is therefore reduced. As solvent, ethanol will also contribute to washing out hydrocarbons 7 in the flow channel 2 downstream of the plug 4. Other metabolic products such as acetate and lactate will also contribute to increased washing-out of hydrocarbons 7 and will increase the degree of production from the reservoir 1.

EXAMPLE 6—A LABORATORY SCALE EXPERIMENT WAS PERFORMED TO SHOW PLUGGING OF A SANDPACK IN ACCORDANCE WITH THE TECHNIQUES OF THE PRESENT INVENTION

Materials and Methods
Bacteria
*Clostridium thermocellum* (CT) JW20; ATCC 31549
Growth Medium CT were cultured according to the methodology described by Freier et al. in Applied and Environmental Microbiology [1988] vol 54, No. 1, p 204-211.

Specifically, the culture medium contained (per liter of deionized water)

1.5 g $KH_2PO_4$
4.2 g $Na_2HPO_4.12H_2O$
0.5 g $NH_4Cl$
0.5 g $(NH_4)_2SO_4$
0.09 g $MgCl_2.6H_2O$
0.03 g $CaCl_2$
0.5 g $NaHCO_3$
2 g of yeast extract
0.5 ml of vitamin solution. The vitamin solution contained (per liter of distilled water)
40 mg of biotin, 100 mg of p-aminobenzoic acid, 40 mg of folic acid, 100 mg of pantothenic acid calcium salt, 100 mg of nicotinic acid, 2 mg of vitamin B12, 100 mg of thiamine hydrochloride, 200 mg of pyridoxine hydrochloride, 100 mg of thioctic acid, and 10 mg of riboflavin.

5 ml of mineral solution. The mineral solution contained (per liter of distilled water)

1.5 g of nitriloacetic acid, 3 g of $MgSO_4$-$7H_2O$, 0.5 g of $MnSO_4$.$H2O$, 1 g of NaCl, 0.1 g of $FeSO_4$ $7H2O$, 0.1 g of $Co(NO_3)_2.6H_2O$, 0.1 g of $CaCl_2$ (anhydrous), 0.1 g of $ZnSO_4.7H_2O$, 50 mg of $NiCl_2$, 10 mg of $CuSO_4*5H_2O$, 10 mg of $AlK_2(SO_4)_3$ (anhydrous), 10 mg of boric acid, 10 mg of $Na_2MoO_4*2H_2O$, 10 mg of $Na_2WO_4$-$2H_2O$, and 1 mg of $Na_2SeO_3$ (anhydrous).

1% cellobiose
Test Set Up

The apparatus was set up to be able to flow growth medium through a sandpack of sandstone size Ø 1-2 mm. A pump was required to deliver pressure up to 20 Bar at maximum head and minimum or zero flow.

The sandpack consisted of a steel 3 m pipe of 1 inch diameter packed with sand—main chemical component $SiO_2$. Upstream of the pump a tank containing dissolved growth media was installed able to maintain 75° C. and to boil. Between the pump and the inlet to the pipe is a return line back to the tank which can reduce flow rate through the pipe. A further valve after the end of the pipe can also be used to adjust flow rate and simulate reservoir conditions with respect to pressure.

Water source: spring water boiled for 1 hour. The detailed chemical content of the water is unknown but the water is characterized as hard, ie containing Calcium. The parts from the tank to the output of the pipe were isolated.

Preparation of the Test System

The system was cleaned by boiled water circulating in the system for 3 hours and de-oxygenated by $N_2$-bubbling. The temperature was lowered to 75° C. in the tank and re-circulated for 1 week. The system was now considered to maintain a steady state with respect to any microbial pollution. Growth medium was circulated for an additional 3 weeks to look for any physical behaviour or change in the packed sand section due to the growth medium.

Observations Prior to Introducing Bacteria:

No pressure built up or change was detected as a result of flooding growth medium through the system over time.

Addition of Bacteria:

A small culture of CT bacteria was inoculated and set to grow in a flask as described in Freier et al. supra, in the growth medium described above. The bacteria were then inserted into the sandpack by opening the pipe near the pump end and infecting a small area. The system for opening was a flanged system.

Analysis

Evaluation was based on visual observations and distillation of water which had passed through the pipe to determine the concentration of ethanol per water unit. Visual observation of gases by testing the flammability of $H_2$ and detection of $CO_2$ concentration were conducted. Gas tests were performed to confirm that the correct pathway was followed. The concentration of ethanol was used as indication of efficiency of bacterial (CT) catabolic processes.

Test Case 1.

The manometer read 10 Bars at the beginning of the test.

Active bacteria were introduced into the sandpack within the growth media. The media was left to grow for 24 hours and a water flow rate of max $20 \times 10^{-6}$ m/s was introduced and the sandpack flooded. This low flow was maintained and adjusted over 2 weeks.

Observation:

After 24 hours the flow rate was reduced. By reducing flow rate using the return line (reject valve), a flow rate of $10 \times 10^{-6}$ m/s was established. The readings on the manometer with closed reject valve (no water using the return line) showed 20 Bars.

The water penetrating trough the sandpack was reduced dramatically, by approx 85-95% and the concentration of ethanol increased 2-fold.

Clear indications are that the flooded sandpacks were blocked. Ethanol production and gas production indicated active, an Cellulosome-pathway.

Test Case 2:

The same test as described in Test case 1 was continued for one month.

The process was in a steady state: No change was observed in pressure, it stayed at approx 20 Bar and there was no change in flow rate or ethanol-production. These results indicate that the plug was maintained.

Test Case 3:

The cellobiose was removed from the growth medium and the system flooded over 7 days.

The pressure decreased and flow rate increased through the sandpack. The pressure dropped to approx 16 Bar. Changes mainly took place in the first 24 hours, from when the changes levelled out to a new steady state situation. Thus, permeability of the plug is increased but some plug structure remains.

Test Case 4:

The complete growth medium was removed and only water provided to flood the system.

The pressure dropped towards 11-12 Bar over 5 days. This suggests the plug is removed/lost or at least that permeability levels return almost to the pre-plug levels.

Test Case 5:

Test case 1 was repeated but with a pipe of 16 inches in diameter.

The results from test 1 were repeated. In this test, a parabolic shape was traced in the sand when opening the sandpack.

Test Case 6:

Test one was repeated and a plug was established. The growth medium was removed and increased flow was introduced until sporous conditions were assumed to have been established. Maximum flow was introduced into the pipe to flush spores in the flow direction. The spores later started to grow and the centre of the plug was observed to settle in the system further into the.

To finish the test, highly alkaline liquid was flushed through the system for 2 days and growth medium was removed. The plug was removed by this treatment.

EXAMPLE 7

Tests were performed in two different setups, one test containing sand infected by oily residues and one test only with sand to investigate bacterial growth in a solid environment.

Test One:

Setup with sand only. The sand was of the same type as described in Example 6. The biological input was based on the Freier tests referenced in Example 6. The water used was taken from the same source and treated the same way, boiled and de-oxygenated. The CT bacteria were grown in bottles and injected into a 1 liter vessel.

The vessel was completely filled with growth medium and bacteria evenly distributed in the medium. The flow was then stopped. Temperature was maintained at approx 60° C.

The microbes grew and catabolised. We could clearly see that the microbes thrived and grew in the sand and by measuring the ethanol content, the tests confirmed metabolic activity.

The Chemostat-test became a static test for 7 days. After 7 days we saw a change in density and noted the colour to be a little darker. We presumed that nutrients were used up and the bugs were in a state of starvation. By flushing growth medium through the sandpack system we were able to change back to a yellowish colour and ethanol was detected.

Test Two:

This test was to establish an environment similar to an empty oil reservoir. This means a sandpack containing 9-16% of oily residues where the residue is mainly located on the lee-side of the sand particles relative to the flooding direction.

A column with sand according to test one was set up. The column was saturated with crude oil from the Statfjord field and flooded with seawater. As a result of the flooding approx 88% of the oil was displaced and the system became water saturated. The system was further flooded 5 times with growth medium and pre-grown CT culture was introduced evenly in the test setup.

The test was set to grow for a week. Corresponding ethanol concentrations to volume of growth medium were measured.

A habitat contaminated by crude oil did not limit the growth and catabolic activity of the culture. It seems the oily parts only displace growth. Therefore growth and metabolic activity can be maintained side by side with an oily environment in a microscale system.

EXAMPLE 8

The Freier approach to CT culturing was modified with bottles containing 3 different fractions of oil. One set of bottles contained 90% of oil, one set of bottles contained 50% of oil and the last set of bottles contained 10% of oil. The remaining liquid contained the Freier medium with cellobiose at 1%. Bottles containing 100% Freier medium with cellobiose (1%) were provided as control. The bottles were shaken every 3 hours during the day. The bottles were opened after 1 week.

Ethanol was produced in concentrations corresponding to the volume and concentration of growth medium.

The oil did not have a inhibiting effect on the culture. The culture does not grow and metabolize within the oily fraction. We concluded that the growth medium was effectively removed in the high concentration of oil due to the fact that oil and water are not soluble. We also concluded that the culture could not utilize Hydrocarbons as carbon-source.

The invention claimed is:

1. A method of establishing a microbial plug in a hydrocarbon-containing geological formation which has been flooded with water, the method comprising:
   a) introducing into the formation a microbial inoculum, the microorganisms of which are:
      (i) in a dormant state,
      (ii) cellulolytic or hemicellulolytic
      (iii) thermophiles, extreme thermophiles or hyperthermophiles,
      (iv) unable to utilise hydrocarbons as a carbon source, and
      (v) not indigenous to the hydrocarbon-containing geological formation;
   b) simultaneously or sequentially introducing into the formation a growth medium which provides a carbon source which can be utilised by the microorganisms introduced in step (a) but not by indigenous microorganisms;
   c) exposing the inoculum to conditions which enable the microorganisms to enter an active growth phase within water channels in the geological formation; and
   d) introducing an injection liquid comprising further growth medium as defined in step b) into the formation via an injection well.

2. The method of claim 1, wherein the inoculum is in the form of spores.

3. A method of maintaining a microbial plug in a hydrocarbon-containing geological formation, said plug comprising microorganisms which are:
   (i) cellulolytic or hemicellulolytic,
   (ii) thermophilic, extreme thermophilic or hyperthermophilic,
   (iii) unable to utilise hydrocarbons as a carbon source, and
   (iv) not indigenous to the hydrocarbon-containing geological formation;
   the method comprising;
   a) flooding the formation with liquid by injecting the liquid into the formation through one or more injection wells, the liquid comprising a growth medium which provides a carbon source which can be utilised by the microorganisms in the plug but not by indigenous microorganisms, and b) continuing the flow of the liquid through the hydrocarbon containing geological formation so that it reaches one or more production wells, thereby maintaining the microbial plug in the hydrocarbon-containing geological formation.

4. The method of claim 3, further comprising the step of monitoring the output of a production well and as a consequence of the properties of the output, adjusting either the concentration of one or more components in the injected liquid or one or more physical properties of the injected liquid.

5. The method of claim 1 or claim 3, wherein the microorganisms are cellulolytic.

6. The method of claim 5, wherein the microorganisms are bacteria or Archaea.

7. The method of claim 6 wherein the microorganisms are *Clostridium thermocellum*.

8. The method of claim 1 or claim 3, wherein the growth medium contains a carbon source selected from the group comprising cellulose, hemicellulose, carboxymethyl cellulose, cellobiose, xylose, xylobiose and xylan.

9. The method of claim 8 wherein the growth medium contains cellobiose.

10. A microbial plug formed in a water flooded petroleum-containing geological formation, characterized in that the plug comprises microorganisms as defined in claim 3.

11. A method of recovering hydrocarbon from a hydrocarbon containing geological formation wherein said method comprises performing a method as claimed in claim 1 or claim 3 and then recovering hydrocarbon from said formation.

12. The method of claim 11, wherein the hydrocarbon is oil.

13. A method for altering in a controlled manner the position and/or extent of an established microbial plug in a hydrocarbon-containing geological formation through which an injection liquid can flow from one or more injection wells to one or more production wells, wherein the microorganisms of the microbial plug are:

(i) cellulolytic or hemicellulolytic,
(ii) thermophilic, extreme thermophilic or hyperthermophilic,
(iii) unable to utilise hydrocarbons as a carbon source, and
(iv) not indigenous to the hydrocarbon-containing geological formation;

the method comprising:

a) selecting an injection liquid and a growth medium which provides a carbon source which can be utilised by the microorganisms of the microbial plug but not the indigenous microorganisms; and b) applying at least one control procedure to said plug using said injection liquid, said control procedure selected from a group comprising pH regulation, temperature regulation, liquid quantity regulation, gas quantity regulation, inhibitor regulation, nutrient quantity regulation, salinity regulation, viscosity regulation, pressure regulation, flowrate regulation, and addition of further microorganisms to the injection liquid; thereby altering in a controlled manner the position and/or extent of the established microbial plug.

14. The method of claim 13 for controlling the length of the established plug in a direction towards at least one injection well, which method comprises:

the control procedure of supplying fresh nutrient to a plug front such that the microorganism can grow into a zone containing nutrient between the plug front and the injection well.

15. The method of claim 13 for controlling the expansion of the spread of the established plug at flanks of the plug, which method comprises:

the control procedure of adding fresh nutrient to the injection water flowing along the flanks of the established plug such that the microorganism can grow into a zone containing nutrient at the flanks of the plug.

16. The method according to claim 14 or 15, which method further comprises pretreating the section at the plug front or at the flank of the plug by at least one of the following control procedures:

flooding the plug front or the flank of the plug with injection liquid containing biocide, in order to reduce the quantity of active endogenous microorganisms;

flooding the plug front or the flank of the plug with injection liquid containing a pH regulator, in order to improve the growth conditions for desired microorganisms;

flooding the plug front or the flank of the plug with injection liquid of low salt content, in order to reduce the salinity in the pore water in the geological formations that surround the plug front and the flank of the plug, so as to improve the growth conditions for desired microorganisms; and flooding the plug front or the flank of the plug with injection liquid in order to cool the geological formations that surround the plug front and the flank of the plug, so as to improve the growth conditions for desired microorganisms.

17. The method of claim 13 for controlling the movement of the established plug front in a direction towards at least one of the production wells, which method comprises:

using a control procedure to supply biocides or other toxic agent to the injection water to a growth-inhibiting or lethal level.

* * * * *